United States Patent [19]
Berrier

[11] Patent Number: 6,133,473
[45] Date of Patent: Oct. 17, 2000

[54] SYNTHESIS OF CARBAMATE COMPOUNDS

[75] Inventor: John Vincent Berrier, Mount Laurel, N.J.

[73] Assignee: Rohm and Haas Company, Philadelphia, Pa.

[21] Appl. No.: 09/302,199

[22] Filed: Apr. 29, 1999

Related U.S. Application Data

[60] Provisional application No. 60/090,581, Jun. 25, 1998.
[51] Int. Cl.$^7$ .......................... C07C 269/02; C07C 271/60
[52] U.S. Cl. ............................................. 560/157
[58] Field of Search ............................................. 560/157

[56] References Cited

U.S. PATENT DOCUMENTS

| | | | |
|---|---|---|---|
| 3,631,155 | 12/1971 | Smiley | 260/77.5 |
| 4,256,841 | 3/1981 | Horacek et al. | 521/51 |

FOREIGN PATENT DOCUMENTS

| | | |
|---|---|---|
| 0014032 A2 | 8/1980 | European Pat. Off. . |
| 0824862 A1 | 2/1998 | European Pat. Off. . |
| WO 97/46517 | 12/1997 | WIPO . |

OTHER PUBLICATIONS

Database Caplus on STN, Acc. No. 1997:295855, Bryld et al., 'Iodopropynyl butylcarbamate: a new contact allergen' Contact Dermatitis (1997), 36(3), p. 156–158 (abstract), 1997.

Database Caplus on STN, Acc. No. 1974:437409, Mori et al., 'Carbamates.' JP 49031638 A2 (abstract), Mar. 22, 1974.

Database Derwent, Acc. No. 1987–038636, Salido Garcia, 'Ketoxime carbamate(s) prepn. –by reacting oxime with aliphatic isocyanates in liq. state in presence of iron (in)organic salts.' IL 64407 A (abstract), Nov. 30, 1986.

Database Caplus on STN, Acc. No. 1982:423316, Salido Garcia, 'Ketoxime carbamates.' ES 497335 (abstract), Jan. 1, 1982.

Chemical Abstracts, vol. 97, No. 3, 1982 XP002116603.

Chemical Abstracts, vol. 120, No. 3, 1993 XP002116602.

"Catalysis of the Isocyanate–Hydroxyl Reaction", J. W. Britain and P. G. Gemeinhardt; Journal of Applied Polymer Science, vol. IV, Issue No. 11, pp. 207–211 (1960).

*Primary Examiner*—Samuel Barts
*Assistant Examiner*—Brian J. Davis
*Attorney, Agent, or Firm*—S. Matthew Cairns; Thomas D. Rogerson

[57] ABSTRACT

Disclosed is a method for the preparation of carbamate compounds substantially free of by-products; the carbamate compounds being prepared by reacting an isocyanate with a hydroxylated compound in the presence of certain catalysts that increase the rate of carbamylation while decreasing the rate of by-product formation.

8 Claims, No Drawings

6,133,473

SYNTHESIS OF CARBAMATE COMPOUNDS

This application claims priority to provisional application No. 60/090,581 filed Jun. 25,1998.

BACKGROUND OF THE INVENTION

This invention relates to a method for preparation of carbamate compounds. In particular, the present invention relates to the use of a certain class of catalysts to increase the rate of carbamate compound formation while greatly decreasing the rate of by-product formation.

Carbamate compounds are a commercially important class of organic compounds. Carbamates are useful as intermediates in the synthesis of a wide variety of organic compounds, such as microbicides, agricultural pesticides and pharmaceutical agents. Many carbamate compounds are themselves known as microbicides, agricultural pesticides and pharmaceutical agents.

Carbamate compounds may be prepared by a variety of methods. Such methods include the reaction of an amide in the presence of an alcohol with a suitable catalyst, the reaction of alcohols with cyanogen halide, the reaction of alkyl hypochlorites with isonitriles, the reaction of haloformates with amines, and the reaction of isocyanates with either oximes or alcohols. Commercially important methods of preparing carbamate compounds are those involving isocyanates. These isocyanate preparations typically require the use of catalysts, such as metal salts, for the reaction to proceed at all and usually result in the presence of significant levels of by-products in the carbamate produced. Much cost and effort must then be spent to purify the resulting carbamate compound.

EP 824 862 A (Hsu et al.) discloses the preparation of certain dihaloformaldoxime carbamates by reacting certain dihaloformaldoximes with suitable isocyanates in the presence of a catalytic amount of dibutyltin dilaurate. While this type of reaction gives the desired carbamates, it is slow, produces low yields and results in a significant amount of by-products. This patent application neither teaches nor discloses other specific catalysts.

EP 014 032 A (Brand et al.) discloses the preparation of iodopropynyl carbamates by reacting an alkynol with an isocyanate, optionally in the presence of a catalyst, followed by iodination. Organic and inorganic basic compounds as well as soluble salts of metals are mentioned generally as possible catalysts. This publication does not disclose that certain catalysts are particularly effective in decreasing by-product formation during carbamate preparation.

There is thus a continuing need for methods of preparing carbamate compounds that are fast, provide high yields and produce very little by-products.

SUMMARY OF THE INVENTION

The present invention is directed to a process for preparing carbamate compounds substantially free of by-products comprising reacting an isocyanate compound with a hydroxylated compound in the presence of a catalyst selected from the group consisting of zinc salts, iron salts, tin dihalide, tin tetrahalide and aluminum acetyl acetonate.

The present invention is also directed to carbamate compounds substantially free of by-products produced by the process as described above.

DETAILED DESCRIPTION OF THE INVENTION

As used throughout the specification, the following terms shall have the following meanings, unless the context clearly indicates otherwise.

"Alkyl," "alkenyl" and "alkynyl" refer to straight chain, branched, or cyclic carbon chains, or any combination thereof. "Halo" and "halogen" refer to fluorine, chlorine, bromine and iodine. "Aryl" refers to phenyl, substituted phenyl, heteroaromatic and substituted heteroaromatic. "Substituted aromatic" means one or more of the hydrogens on the aromatic ring are replaced by another substituent, such as cyano, hydroxy, $(C_1-C_4)$alkyl, nitro, mercapto, $(C_1-C_4)$alkylthio, halo and $(C_1-C_4)$alkoxy. "Substituted alkyl," "substituted alkenyl" and "substituted alkynyl" mean one or more of the hydrogens on the carbon chain are replaced by another substituent, such as cyano, hydroxy, $(C_1-C_4)$alkyl, nitro, mercapto, $(C_1-C_4)$alkylthio, halo and $(C_1-C_4)$alkoxy. "Substituted aralkyl" means one or more hydrogens on the aromatic ring or alkyl chain are replaced by another substituent, such as cyano, hydroxy, $(C_1-C_4)$alkyl, nitro, mercapto, $(C_1-C_4)$alkylthio, halo and $(C_1-C_4)$alkoxy. "Heteroaromatic" refers to a 5–7 membered aromatic ring having one or more heteroatoms in the ring. "Substituted heteroaromatic" means one or more of the hydrogens on the aromatic ring are replaced by another substituent, such as cyano, hydroxy, $(C_1-C_4)$alkyl, nitro, mercapto, $(C_1-C_4)$alkylthio, halo and $(C_1-C_4)$alkoxy.

All amounts are percent by weight ("% wt"), unless otherwise noted. All ranges are inclusive. As used throughout the specification, the following abbreviations are applied: g=gram; mg=milligram; C=Centigrade; mL=milliliter; mol=mole; mmol=millimoles; mm=millimeter; v=volume; and GC=gas chromatography.

The present invention is directed to the surprising discovery that the use of certain types of catalysts in the preparation of carbamate compounds from isocyanate compounds results in increased yields of the carbamate with substantially no by-product formation. The process of the present invention may be used to prepare any carbamate compound made from an isocyanate compound. Suitable carbamates that can be prepared by the process of the present invention include, but are not limited to: iodopropynyl butylcarbamate; N-methyl-dibromoformaldoxime carbamate; N-(2-chloroethyl)-dibromoformaldoxime carbamate; N-(4-chlorophenyl)-dibromoformaldoxime carbamate; N-(2,4-dichlorophenyl)-dibromoformaldoxime carbamate; N-ethyl-dibromoformaldoxime carbamate; N-(n-butyl)-dibromoformaldoxime carbamate; N-(n-octyl)-dibromoformaldoxime carbamate; N-(n-hexyl)-dibromoformaldoxime carbamate; and N-(4-methylphenyl)-dibromoformaldoxime carbamate.

Any isocyanate compound that reacts with a hydroxylated compound is useful in the present invention. The isocyanate compounds may be aliphatic, aromatic, substituted aromatic, heteroaromatic or substituted heteroaromatic. Suitable aliphatic isocyanates include, but are not limited to: $(C_1-C_{12})$ alkylisocyanates, substituted $(C_1-C_{12})$alkylisocyanates, $(C_2-C_{12})$alkenylisocyanates, substituted $(C_2-C_{12})$ alkenylisocyanates, $(C_2-C_{12})$alkynylisocyanates, substituted $(C_2-C_{12})$alkenylisocyanates, $(C_7-C_{12})$ aralkylisocyanates, and substituted $(C_7-C_{12})$ aralkylisocyanates. Examples of isocyanates useful in the present invention include, but are not limited to: phenylisocyanate, benzylisocyanate, methylisocyanate, ethylisocyanate, butylisocyanate, 2,6-dichlorophenylisocyanate.

The hydroxylated compounds useful in the present invention are any compounds that contain a hydroxyl group and will react with an isocyanate compound. Such hydroxylated compounds include alcohols and oxime compounds. Suitable alcohols useful in the present invention include, but are not limited to: $(C_1-C_{12})$alkanols, halo$(C_1-C_{12})$alkanols, $(C_2-C_{12})$alkenols, halo$(C_2-C_{12})$alkenols, $(C_2-C_{12})$alkynols, halo$(C_2-C_{12})$alkynols, $(C_1-C_{12})$aralkanols, halo$(C_1-C_{12})$aralkanols, phenol, substituted phenol, isothiazole, substituted isothiazole, naphthol, and substituted naphthol. Preferred alcohols include: methanol, ethanol, propanol, butanol, benzyl alcohol, phenethyl alcohol, propynyl alcohol, halopropynyl alcohol, and allyl alcohol.

It is preferred that the hydroxylated compound is an oxime compound. Any oxime compound is useful in the present invention as long as it reacts with an isocyanate compound. Suitable oxime compounds useful in the present process include, but are not limited to: formaldoxime, haloformaldoxime, dihaloformaldoxime, halo(hydroxyimino)acetic acid, halo(hydroxyimino)acetic acid $(C_1-C_8)$alkyl ester, 1-halo-1-(hydroxyimino)-2-$(C_1-C_8)$ alkanone, haloglyoxime, dihaloglyoxime, dialkyl ketone oxime, diaryl ketone oxime, alkyl aryl ketone oxime, alkyl aldehyde oxime, and aryl aldehyde oxime. It is preferred that the oxime is a halooxime, and more preferably a dihalooxime.

The amount of the isocyanate compound and hydroxylated compound useful in the present invention depend upon the particular carbamate to be prepared. Typically, the amount of the isocyanate compound is from 0.75 to 2.5 mole equivalents of the hydroxylated compound, and preferably 0.8 to 1.5 mole equivalents.

The process of the present invention may be carried out in a solvent selected from the group consisting of halogenated aliphatics, carbonates, aromatics and haloaromatics. Carbonate solvents may be either alkylenecarbonates or dialkylcarbonates. Suitable solvents include, but are not limited to: methylene dichloride, methylene dibromide, ethylene dichloride, ethylene dibromide, methyliodide, chloroform, bromoform, carbon tetrachloride, carbon tetrabromide, benzene, chlorobenzene, dichlorobenzene, toluene, benzotrifluoride, chlorotoluene, diethylcarbonate, ethylenecarbonate, dimethylcarbonate and propylenecarbonate. Methylene dichloride, methylene dibromide, toluene and benzotrifluoride are preferred.

Where the isocyanate compound or the hydroxylated compound is liquid at the reaction temperature, such material may be used as the solvent for the reaction. It is preferred that a separate solvent be added to the reaction.

The catalysts useful in the process of the present invention are zinc salts, iron salts, tin dihalide, tin tetrahalide and aluminum acetyl acetonate. Suitable zinc salts and iron salts include, but are not limited to: zinc dibromide, zinc dichloride, zinc neodecanoate, zinc stearate, zinc acetyl acetonate, zinc trifluoromethane-sulfonate, zinc 2-ethylhexanoate, zinc acetate, zinc trifluoroacetate, zinc hexafluoro acetyl acetonate, zinc oxide, ferric tribromide, ferrous dibromide, ferric trichloride, ferrous dichloride and ferric acetyl acetonate.

Preferred catalysts are those that provide carbamate compounds substantially free of by-products as well as provide for fast rates of carbamate compound formation. By substantially free of by-products is meant carbamate compounds having less than 1% wt of by-products, based on the weight of the carbamate compound, preferably less than 0.1% wt. The preferred catalysts are zinc dibromide, zinc neodecanoate, zinc acetyl acetonate, zinc 2-ethylhexanoate, zinc acetate, ferric tribromide and ferrous dibromide. Of these preferred catalysts, zinc salts are most preferred.

The amount of catalyst useful in the process of the present invention depends upon the particular isocyanate compound and the particular hydroxylated compound. Any amount of catalyst may be used up to the solubility limit of the particular catalyst in the solvent of the reaction. Typically, the amount of catalyst is 0.01 to 5% wt, based on the combined weight of the isocyanate compound and the hydroxylated compound. It is preferred that the amount of catalysts is 0.05 to 4% wt, and more preferably 0.1 to 3% wt. For example, when the hydroxylated compound is an oxime, the amount of catalyst is typically 0.5 to 4% wt. When the hydroxylated compound is an alcohol, the amount of the catalyst is typically 0.01 to 3% wt.

The catalysts useful in the present invention are commercially available, such as from Alfa Aesar (Ward Hill, Mass.) and may be used without further purification.

The isocyanate compound, hydroxylated compound, solvent and catalyst may be combined in any order. It is preferred that the solvent be added to the reaction vessel first, followed by the hydroxylated compound, the catalyst and then the isocyanate. When the hydroxylated compound is a solid, it is preferred that either the solvent be added to the vessel before addition of the hydroxylated compound or the hydroxylated compound be first dissolved in the solvent before being added to the reaction vessel.

The process of the present invention may be carried out at a wide range of temperatures. In general, the present process may be performed at a temperature in the range of $-10°$ to $100°$ C. It is preferred that the temperature of the reaction be in the range of $-5°$ to $65°$ C., and more preferably in the range of $0°$ to $35°$ C.

The rate of reaction of the present process depends on catalyst concentration. Increasing the concentration of the catalyst will increase the rate of reaction, resulting in a shorter reaction time. Decreasing the concentration of the catalyst will decrease rate of reaction and result in a longer reaction time. It is preferred that the reaction be at least 10 percent completed within 0.5 hours and 20 percent within 16 hours of reaction time when 2% wt of catalyst is used. It is more preferred that the reaction be 85 percent completed within 0.5 hours, and especially preferred that the reaction be 90 percent completed within 0.5 hours when 2% wt of catalyst is used.

The carbamate compounds produced by the process of the present invention may be separated from the reaction mixture by any known method, such as filtration, evaporation, extraction, and the like. The resulting carbamates may be used without further purification.

One advantage of the present process is that carbamate compounds produced by this process have significantly lower levels of by-products than carbamates produced by known methods. Another advantage of the present process is the greatly increased rate of carbamate compound formation compared to known methods. For example, the process of preparing carbamate compounds from certain oxime compounds is generally quite slow. When the catalysts of the present invention are employed in the process, the rate of carbamate compound formation is greatly increased. Thus, the process of the present invention provides carbamate compounds in purer form and in less time than previously known methods of preparation.

It is known to use a variety of metal salt catalysts in the preparation of carbamates from isocyanates. For example, see Britain et al., "Catalysis of the Isocyanate-Hydroxyl Reaction," *Journal of Applied Polymer Science*, Vol. IV, no. 11, pp. 207–211 (1960), for a wish list of catalysts that can be used in this type of reaction. This article discusses only the rate of carbamate formation in terms of gelation time of the reaction mixture. This article does not recognize that certain metal salt catalysts can provide carbamate compounds that are substantially free of by-products.

The following examples are presented to illustrate further various aspects of the present invention, but are not intended to limit the scope of the invention in any aspect.

EXAMPLE 1

This Example demonstrates the effectiveness of the catalysts of the present invention.

To a 50 mL three-neck, round bottom flask equipped with a stir bar and a nitrogen atmosphere was charged 1 g (4.9 mmol) of dibromoformaldoxime. To this was added 10 g of methylene dichloride containing 2% wt of appropriate catalyst. The mixture was stirred until all the solids dissolved. To the flask was then added 0.49 g (4.9 mmol) of n-butyl isocyanate. The reaction mixture was stirred at room temperature.

Aliquots (50 mg) of the reaction mixture were taken after 0.5 and 16 hours of reaction. The aliquots were quenched with 20 mL of a 50/50 v/v mixture of hexane/ethyl acetate. The quenched aliquots were analyzed by GC to determine the percentage of N-butyl dibromoformaldoxime carbamate and by-products formed. The identity of the N-butyl dibromoformaldoxime carbamate and by-products was confirmed by comparison to analytical standards of the compounds.

The catalysts tested are reported in Table 1, along with the percentage of carbamate formed and the percentage of by-products. By-product 1 is dibutyl urea and By-product 2 is tributyl biuret.

TABLE 1

Percentage of Carbamate Formed

| Catalyst | 0.5 Hours | 16 Hours | By-product 1 (%) | By-product 2 (%) |
|---|---|---|---|---|
| Invention | | | | |
| Zinc dibromide | 88.4 | 99.7 | 0 | 0 |
| Zinc neodecanoate | 89.7 | 98.8 | 0 | 0 |
| Zinc Stearate | 84.3 | 98.6 | 0 | 0 |
| Ferric tribromide | 91.1 | 98.4 | 0 | 0 |
| Zinc acetyl acetonate | 91.2 | 98.3 | 0 | 0 |
| Zinc trifluoromethane-sulfonate | 68.7 | 98.3 | 0 | 0 |
| Tin (II) bromide | 78.3 | 98.0 | 0 | 0 |
| Ferrous dibromide | 89.0 | 97.9 | 0 | 0 |
| Zinc 2-ethylhexanoate | 86.0 | 97.9 | 0 | 0 |
| Iron (III) acetyl acetonate | 81.9 | 97.8 | 0 | 0 |
| Tin (IV) bromide | 65.4 | 97.2 | 0 | 0 |
| Zinc acetate | 84.9 | 96.0 | 0 | 0 |
| Zinc trifluoroacetate | 68.4 | 92.6 | 0 | 0 |
| Ferric chloride | 87.1 | 91.0 | 0 | 0 |
| Ferric trifluoride | 12.3 | 24.0 | 0 | 0 |
| Zinc chloride | 78.4 | 83.5 | 0 | 0 |
| Zinc hexafluoro-acetyl acetonate | 30.9 | 76.4 | 0 | 0 |
| Aluminum acetyl acetonate | 6.1 | 39.8 | 0 | 0 |
| Zinc oxide | 39.9 | 97.4 | 0 | 0 |
| Comparative | | | | |
| Tin, dibutyl dilaurate | 60.2 | 73.9 | 0.6 | 1.6 |
| Tin (II) octoate | 66.1 | 90.9 | 4.6 | 0.6 |
| Tin oxide, dibutyl | 61.7 | 89.4 | 6.0 | 0.7 |
| Tin, dibutyl bis mercaptide | 62.1 | 85.7 | 6.4 | 1.5 |
| Titanium tetra-ethoxide | 29.9 | 94.1 | 1.6 | 0.5 |
| Titanium tetra-isopropoxide | 13.5 | 91.7 | 2.5 | 0.5 |

TABLE 1-continued

Percentage of Carbamate Formed

| Catalyst | 0.5 Hours | 16 Hours | By-product 1 (%) | By-product 2 (%) |
|---|---|---|---|---|
| Tin, dibutyl dimethoxide | 88.3 | 91.0 | 3.4 | 0.5 |
| Triethylamine | 3.5 | 6.9 | 0 | 0 |
| Titanium ethoxy-isopropoxy-bis-acetyl acetonate | 11.5 | 59.0 | 14.9 | 5.4 |
| Formic acid | 4.0 | 40.0 | 5.4 | 2.9 |
| Zirconium acetyl acetonate | 1.1 | 31.8 | 8.0 | 3.4 |
| Bismuth triacetate | 18.7 | 27.1 | 4.2 | 7.0 |
| Tin, tributyl acetate | 11.1 | 26.3 | 0.7 | 6.7 |
| Dimethylaminopyridine | 0 | 23.8 | 0 | 0 |
| Acetic acid | 17.5 | 20.4 | 6.9 | 5.2 |
| 2-Pyridone | 0 | 2.2 | 0 | 0.5 |
| Tin, tributyl methoxide | 0.0 | 18.3 | 0 | 2.4 |
| DBU | 2.9 | 17.1 | 0 | 0.4 |
| Chloroacetic acid | 10.5 | 14.2 | 2.8 | 4.2 |
| Tetramethyl guanidine | 0 | 12.6 | 0 | 0 |
| Aluminum chloride | 0.7 | 11.4 | 0 | 0 |
| Polyvinylpyridine | 0 | 0 | 0 | 0 |

These data clearly show that the catalysts of the invention provide for quick carbamate formation without the generation of by-products.

EXAMPLE 2

This Example shows the range of catalyst amount useful in the present invention.

The process of Example 1 was repeated using the catalysts listed in Table 2 in the amounts shown. Aliquots of the reaction were taken and analyzed according to Example 1. The percentages of carbamate and by-products formed are reported in Table 2.

TABLE 2

Percentage of Carbamate Formed

| Catalyst | 0.5 Hours | 16 Hours | By-product 1 (%) | By-product 2 (%) |
|---|---|---|---|---|
| Invention | | | | |
| 0.5% wt Zinc acetyl acetonate | 73.2 | 95.9 | 0 | 0 |
| 2.0% wt Zinc acetyl acetonate | 91.2 | 98.3 | 0 | 0 |
| Comparative | | | | |
| 0.5% wt Tin, dibutyl dimethoxide | 29.3 | 66.3 | 1.9 | 0.8 |
| 2.0% wt Tin, dibutyl dimethoxide | 88.3 | 91.0 | 3.4 | 0.5 |
| 1.0% wt Tin, dibutyl dilaurate | 53.7 | NA* | 1.1 | 0.4 |
| 2.0% wt Tin, dibutyl dilaurate | 60.2 | 73.9 | 0.6 | 1.6 |
| 4.0% wt Tin, dibutyl dilaurate | 74.4 | 88.3 | 5.1 | 0.7 |

*NA = not analyzed

These data show that 0.5% wt of zinc acetyl acetonate provides a purer carbamate in higher yield than other known catalysts.

EXAMPLE 3

This Example demonstrates some of the solvents useful in the present invention.

The process of Example 1 was repeated using zinc acetyl acetonate as the catalyst using the solvents listed in Table 3. Aliquots of the reaction were taken after 0.5 and 16 hours of reaction. The aliquots were analyzed by GC for the amount of carbamate compound formed. These results are reported in Table 3.

TABLE 3

Percentage of Carbamate Formed

| Solvent | 0.5 Hours | 16 Hours |
|---|---|---|
| Invention | | |
| Methylene chloride | 91.2 | 98.3 |
| Ethylene dichloride | 74.6 | 98.0 |
| Methylene bromide | 89.7 | 97.0 |
| Benzotrifluoride | 81.2 | 96.9 |
| Toluene | NA* | 96.9 |
| Chlorobenzene | 66.4 | 88.2 |
| Carbon tetrachloride | 43.5 | 83.6 |
| Diethyl carbonate | 38.6 | 81.5 |
| Comparative | | |
| Ethyl acetate | 5.3 | 71.9 |
| 2-Butanone | 1.4 | 46.8 |
| Acetonitrile | 4.6 | 32.6 |
| Acetone | 0 | 28.8 |
| Dimethoxymethane | 6.4 | 18.5 |

*NA = not analyzed

These data show that certain classes of solvents are useful for the process of the present invention.

EXAMPLE 4

This Example shows the preparation of N-n-butyl dibromoformaldoxime carbamate using a catalyst of the invention.

To a 500 mL 3 neck jacketed round-bottomed flask equipped with a magnetic spin bar, a thermometer, an addition funnel, and an inert atmosphere, was added a solution of dibromoformaldoxime (50.0 g, 0.247 mol) in methylene dichloride (250 g). To this stirred solution was added 1.49 g of zinc acetyl acetonate hydrate as a catalyst, followed by addition of 24.5 g (0.247 mol) of n-butyl isocyanate from an addition funnel while maintaining the temperature of the reaction at 0–5° C. The reaction mixture was further stirred at room temperature for 16 hours. The reaction mixture was then washed with 5% sodium bicarbonate (2×175 g) and de-ionized water (2–175 g). The organic layer was dried over anhydrous $MgSO_4$, filtered and concentrated on a rotary evaporator to give a yellow oil of 94.9% purity (70.0 g, 0.220 mol, 89.1% yield). NMR ($CDCl_3$) δ0.95 (t, 3 H); 1.38 (m, 2 H); 1.56 (m, 2 H); 3.31 (t, 2 H); 5.73 (s, 1 H). The product was also analyzed without further purification for by-products and was found to contain 0% of By-product 1 and 0% of By-product 2.

These data show that the process of the present invention provides carbamate compounds in high yields in short reaction times and produces no by-products.

EXAMPLE 5 (COMPARATIVE)

This Example shows the preparation of N-n-butyl dibromoformaldoxime carbamate according to EP 824862 (Hsu et al.).

To a 300 mL 3 neck round bottom flask equipped with a magnetic stir bar and an inert atmosphere was added 50.7 g (0.25 mol) of dibromoformaldoxime and 100 mL of methylene dichloride with cooling in an ice bath to 2° C. n-Butyl isocyanate (24.8 g, 0.25 mol) was then added dropwise, followed by 30 drops of dibutyltin dilaurate (1.58 g, 0.0025 mol) as catalyst. The reaction mixture was further stirred at room temperature for 41 hours, until the ratio of carbamate product to formaldoxime was greater than 15:1 as measured by GC. The mixture was washed with 5% sodium bicarbonate solution (2×250 mL) and water (2×250 mL). The organic layer was dried over $MgSO_4$ and filtered. The filtrate was concentrated under vacuum on a rotary evaporator to give 60.4 g (80% crude yield) of a yellow oil of about 80% purity. A purer (98.5%) light yellow oil, 49.5 g (66% purified yield), was obtained by column chromatography using silica gel and eluting with hexane/ethyl acetate (80/20 v/v). NMR ($CDCl_3$) δ0.95 (t, 3 H); 1.38 (m, 2 H); 1.56 (m, 2 H); 3.31 (t, 2 H); 5.73 (s, 1 H). The purified product was also analyzed for by-products and was found to contain 0.6% of By-product 1 and 1.6% of By-product 2.

Comparison of the results of Example 4 with Example 5 indicate that the previously known methods of preparing carbamate compounds are slow, produce low yields and contain significant amounts of by-products, whereas the present process is fast, and results in high yields of carbamate compounds without by-products.

What is claimed is:

1. A process for preparing carbamate compounds substantially free of by-products comprising reacting aliphatic, aromatic, substituted aromatic heteroaromatic, or substituted heteroaromatic isocyanate compound with an alcohol or oxime compound in the presence of a catalyst selected from the group consisting of zinc dibromide, zinc dichloride, zinc neodecanoate, zinc stearate, zinc acetyl acetonate, zinc trifluoromethane-sulfonate, zinc 2-ethylhexanoate, zinc acetate, zinc trifluoroacetate, zinc hexafluoro acetyl acetonate, zinc oxide, ferric acetylacetonate, ferric tribromide, ferrous dibromide, tin dihalide, and tin tetrahalide.

2. The process according to claim 1 wherein the zinc and iron salts are selected from the group consisting of zinc dibromide, zinc neodecanoate, zinc acetyl acetonate, zinc2-ethylhexanoate, zinc acetate, ferric tribromide, and ferrous dibromide.

3. The process according to claim 1 wherein the catalyst is present in an amount of 0.01 to 5% wt, based on the combined weight of the isocyanate compound and the hydroxylated compound.

4. The process according to claim 1 further comprising a solvent selected from the group consisting of halogenated aliphatics, carbonates, aromatics and haloaromatics.

5. The process according to claim 1 wherein the alcohol is selected from the group consisting of ($C_1$–$C_{12}$)alkanols, halo($C_2$–$C_{12}$)alkanols, ($C_2$–$C_{12}$)alkenols, halo($C_2$–$C_{12}$)alkenols, ($C_2$–$C_{12}$)alkynols, halo($C_2$–$C_{12}$)alkynols, ($C_1$–$C_{12}$)aralkanols, halo($C_1$–$C_{12}$)aralkanols, phenol, substituted phenol, isothiazole, substituted isothiazole, naphthol, and substituted naphthol.

6. The process according to claim 1 wherein the oxime is selected from the group consisting of formaldoxime, haloformaldoxime, dihaloformaldoxime, halo(hydroxyimino)acetic acid, halo(hydroxyimino)acetic acid ($C_1$–$C_8$)alkyl ester, 1-halo-1-(hydroxyimino)-2-($C_1$–$C_8$) alkanone, haloglyoxime, dihaloglyoxime, dialkyl ketone oxime, diaryl ketone oxime, alkyl aryl ketone oxime, alkyl aldehyde oxime, and aryl aldehyde oxime.

7. The process according to claim 1 wherein the carbamate compound is selected from the group consisting of: iodopropynyl butylcarbamate; N-methyl-dibromoformaldoxime carbamate; N-(2-chloroethyl)-dibromoformaldoxime carbamate; N-(4-chlorophenyl)-dibromoformaldoxime carbamate; N-(2,4-dichlorophenyl)-dibromoformaldoxime carbamate; N-ethyl-dibromoformaldoxime carbamate; N-(n-butyl)- dibromoformaldoxime carbamate; N-(n-octyl)-dibromoformaldoxime carbamate; N-(n-hexyl)-dibromoformaldoxime carbamate; and N-(4-methylphenyl)-dibromoformaldoxime carbamate.

8. The process according to claim 1 wherein the isocyanate compound is selected from the group consisting of $(C_1-C_{12})$alkylisocyanates, substituted $(C_1-C_{12})$alkylisocyanates, $(C_2-C_{12})$alkenylisocyanates, substituted $(C_2-C_{12})$alkenylisocyanates, $(C_2-C_{12})$alkynylisocyanates, substituted $(C_2-C_{12})$alkenylisocyanates, $(C_7-C_{12})$aralkylisocyanates, and substituted $(C_7-C_{12})$aralkylisocyanates.

* * * * *